United States Patent [19]

Wehinger et al.

[11] Patent Number: 4,622,332
[45] Date of Patent: Nov. 11, 1986

[54] ASYMMETRIC DIESTERS OF HANTZSCH DIHYDROPYRIDINES WITH HYPOTENSIVE ACTIVITY

[75] Inventors: Egbert Wehinger; Horst Meyer; Andreas Knorr, all of Wuppertal, Fed. Rep. of Germany

[73] Assignee: Bayer Aktiengesellschaft, Leverkusen, Fed. Rep. of Germany

[21] Appl. No.: 468,621

[22] Filed: Feb. 22, 1983

[30] Foreign Application Priority Data

Mar. 10, 1982 [DE] Fed. Rep. of Germany ....... 3208628

[51] Int. Cl.$^4$ .................. C07D 211/86; A61K 31/455
[52] U.S. Cl. .................................. 514/356; 546/321; 546/281; 546/278; 546/284; 546/283; 546/257; 546/144; 546/167; 546/271; 544/238; 544/333; 544/405
[58] Field of Search ............... 544/116, 119, 120, 122, 544/128, 130, 131, 238, 284, 333, 353, 405; 546/144, 147, 167, 251, 270, 271, 273, 275, 278, 279, 281, 283, 284, 321, 280; 424/248.5, 248.51, 248.55, 250, 258, 251, 266; 514/356

[56] References Cited

U.S. PATENT DOCUMENTS

| | | | |
|---|---|---|---|
| 3,799,934 | 3/1974 | Meyer et al. | 260/294.8 G |
| 3,867,393 | 2/1975 | Meyer et al. | 260/294.9 |
| 3,883,540 | 5/1975 | Meyer et al. | 546/321 |
| 3,932,645 | 1/1976 | Meyer et al. | 424/266 |
| 4,258,042 | 3/1981 | Loev et al. | 424/248.5 |
| 4,307,103 | 12/1981 | Sato et al. | 424/266 |

FOREIGN PATENT DOCUMENTS

| | | | |
|---|---|---|---|
| 934758 | 10/1973 | Canada | 260/294.2 |
| 0039863 | 11/1981 | European Pat. Off. | |
| 2847236 | 5/1980 | Fed. Rep. of Germany | 514/356 |
| 740768 | 11/1972 | U.S.S.R. | |

OTHER PUBLICATIONS

German Chem. E. Knoevenagel, vol. 31, pp. 738–749.
Stradins, J. et al., "Voltammetry of 1,4 Dihydropyridine Derivatives", Khim. Geterotsikl. Soedin. (1972)—Chem. Abst. 76:139832k.
Vigante, B. et al., "2,6–Dimethyl–1,4–Dihydropyridine-3,5-Dicarboxylic acid Esters" (1980)—Chem. Abstracts 93:168145v.
Russian Article, 1972, No. 1, pp. 81–87.
Board of Appeals decision 4/22/83, Appeal No. 535-20, Paper No. 2.

*Primary Examiner*—Henry R. Jiles
*Assistant Examiner*—Dale A. Bjorkman
*Attorney, Agent, or Firm*—Sprung Horn Kramer & Woods

[57] ABSTRACT

Compounds of the formula

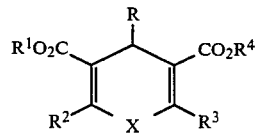

in which

R is an optionally substituted aryl or heterocyclic radical, $R^1$ is a hydrocarbon radical which is optionally interrupted by 1 oxygen atom in the chain, and/or which is optionally substituted, $R^4$ is an aliphatic hydrocarbon radical having 7 to 14 carbon atoms, which is optionally interrupted by one oxygen atom and/or which is optionally substituted, $R^2$ and $R^3$ each independently is hydrogen, an alkyl radical, an aryl radical or an aralkyl radical, or, for the case where one of the substituents $R^2$ or $R^3$ has the above-mentioned meaning, the other is hydroxymethyl, acetoxymethyl or amino, and X is N-$R^5$, wherein $R^5$ is hydrogen, an alkyl radical which is optionally interrupted by an oxygen atom, a morpholinoalkyl radical, an aryl radical or an aralkyl radical or X is an oxygen atom, when one of the radicals $R^2$ or $R^3$ denotes an amino group, or pharmaceutically acceptable acid addition salts thereof, exhibit hypotensive activity.

12 Claims, No Drawings

ASYMMETRIC DIESTERS OF HANTZSCH DIHYDROPYRIDINES WITH HYPOTENSIVE ACTIVITY

The present invention relates to new compounds having lasting circulatory effects, several processes for their preparation and their use as medicaments having circulatory effects, in particular as hypotensive agents.

It has already been disclosed that diethyl 1,4-dihydro-2,6-dimethyl-4-phenylpyridine-3,5-dicarboxylate is obtained when ethyl 2-benzylideneacetoacetate is reacted with ethyl β-aminocrotonate or ethyl acetoacetate and ammonia (E. Knoevenagel, Ber. dtsch. chem. Ges. 31, 743 (1898)).

Furthermore it is known that certain 1,4-dihydropyridines exhibit interesting pharmacological properties (F. Bossert and W. Vater, Naturwissenschaften 58, 578 (1971)).

Furthermore, it has been disclosed in German Offenlegungsschriften (German Published Specifications) Nos. 2,117,571 and 2,117,573 that similar compounds can be used as coronary agents and as hypotensive agents.

However, knowing this state of the art, it could not be expected that the new compounds according to the invention would have such a surprisingly lasting hypotensive effect.

The invention relates to new compounds of the general formula (I)

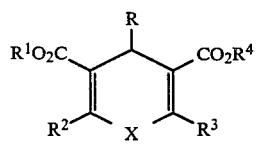

in which
R represents aryl or thienyl, furyl, pyrryl, pyrazolyl, imidazolyl, oxazolyl, isoxazolyl, thiazolyl, pyridyl, pyridazinyl, pyrimidyl, pyrazinyl, indolyl, benzimidazolyl, benzoxazolyl, benzisoxazolyl, benzoxadiazolyl, quinolyl, isoquinolyl, quinazolyl or quinoxalyl, the aryl radical and the heterocycles optionally containing 1 to 2 identical or different substituents from the group comprising phenyl, alkyl, alkoxy, alkylene, dioxyalkylene, halogen, trifluoromethyl, polyfluoroalkoxy, nitro, cyano, azido or $SO_m$-alkyl (m=0 to 2), $R^1$ represents a straight-chain, branched or cyclic, saturated or unsaturated hydrocarbon radical, which is optionally interrupted by 1 oxygen atom in the chain, and/or which is optionally substituted by halogen, cyano, hydroxyl, acyloxy, phenyl, phenoxy, or by an amino group which in turn is optionally substituted by 2 identical or different substituents from the group comprising alkyl, aryl or aralkyl, $R^4$ represents a straight-chain, branched or cyclic, saturated or unsaturated aliphatic hydrocarbon radical having 7 to 14 carbon atoms, which is optionally interrupted by one oxygen atom and/or which is optionally substituted by halogen, hydroxyl or acyloxy, $R^2$ and $R^3$ are identical or different and each represent hydrogen, a straight-chain or branched alkyl radical, an aryl radical or an aralkyl radical, or, for the case where one of the substituents $R^2$ or $R^3$ has the abovementioned meaning, the other represents hydroxymethyl, acetoxymethyl or amino, and X represents N-$R^5$, wherein $R^5$ represents hydrogen, a straight-chain or branched alkyl radical, which is optionally interrupted by an oxygen atom, a morpholinoalkyl radical, an aryl radical or an aralkyl radical or X represents an oxygen atom, when one of the radicals $R^2$ or $R^3$ denotes an amino group, and their pharmaceutically acceptable acid addition salts.

The preparation of the compounds according to the invention can be carried out by several processes, which are essentially derived from the known Hantzsch pyridine synthesis. Depending on the type of the various meanings for the substituents, the subvariants of this synthetic route are described in the following text. The variants (A) to (G) each refer to the preparation of dihydropyridines. The variant H relates to a subsequent exchange of substituents in the 2-position of the dihydropyridine ring and variant J relates to the preparation of 4H-pyrans.

In the case where X in the general formula (I) represents N-$R^5$, wherein $R^5$ has the abovementioned meaning, and $R^{2'}$ and $R^{3'}$ each represent hydrogen, a straight-chain or branched alkyl radical, an aryl radical, an aralkyl radical or the acetoxymethyl group, the preparation of the compounds according to the invention is preferably carried out by (A) reacting ylidene- β-ketoesters of the general formula (II)

in which
R, $R^1$ and $R^{2'}$ have the abovementioned meaning, with enaminocarboxylates of the general formula (III)

in which
$R^{3'}$, $R^5$ and $R^4$ have the abovementioned meaning, optionally in the presence of inert organic solvents, or (B) reacting ylidene- β-ketoesters of the general formula (II)

in which R, $R^1$ and $R^{2'}$ have the abovementioned meaning, with amines of the general formula (IV) and β-ketocarboxylates of the general formula (V)

in which $R^5$, $R^{3'}$ have the abovementioned meaning, optionally in the presence of inert organic solvents, or
(C) reacting ylidene- β-ketoesters of the general formula (VI)

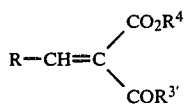 (VI)

in which R, $R^{3'}$ and $R^4$ have the abovementioned meaning, with enaminocarboxylates of the general formula (VII)

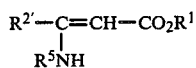 (VII)

in which $R^{2'}$, $R^5$ and $R^1$ have the abovementioned meaning, optionally in the presence of inert organic solvents, or (D) reacting ylidene- $\beta$-ketoesters of the general formula (VI)

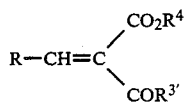 (VI)

in which R, $R^{3'}$ and $R^4$ have the abovementioned meaning, with amines of the general formula (IV)

 (IV)

in which $R^5$ has the abovementioned meaning, and $\beta$-ketocarboxylates of the general formula (VIII)

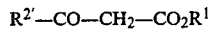 (VIII)

in which $R^{2'}$ and $R^1$ have the abovementioned meaning, optionally in the presence of inert organic solvents or (E) reacting aldehydes of the general formula (IX)

 (IX)

in which R has the abovementioned meaning, with enaminocarboxylates of the general formula (III)

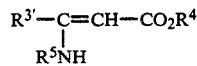 (III)

in which $R^{3'}$, $R^4$ and $R^5$ have the the abovementioned meaning, and with $\beta$-ketocarboxylates of the general formula (VIII)

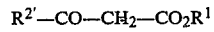 (VIII)

in which $R^1$ and $R^{2'}$ have the abovementioned meaning, optionally in the presence of inert organic solvents, or (F) reacting aldehydes of the general formula (IX)

 (IX)

in which R has the abovementioned meaning, with enaminocarboxylates of the general formula (VII)

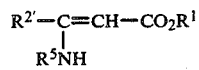 (VII)

in which $R^1$, $R^{2'}$ and $R^5$ have the abovementioned meaning, and with $\beta$-ketocarboxylates of the general formula (V)

$$R^{3'}-CO-CH_2-CO_2R^4 \quad (V)$$

in which $R^{3'}$ and $R^4$ have the abovementioned meaning, optionally in the presence of inert organic solvents, or (G) in the case where X in formula (I) denotes NH and $R^2$ or $R^3$ represent an amino group, the compounds according to the invention are preferably prepared by 1. Reacting ylidene- $\beta$-ketoesters of the general formula (II)

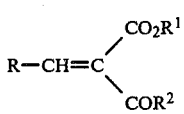 (II)

in which
R, $R^1$ and $R^2$ have the abovementioned meaning, but $R^2$ does not represent an amimo or hydroxymethyl group,
with amidinoacetates of the general formula (X)

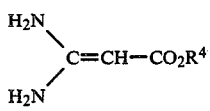 (X)

in which $R^4$ has the abovementioned meaning, optionally in the presence of inert organic solvents or 2. Reacting ylidene- $\beta$-ketoesters of the general formula (VI)

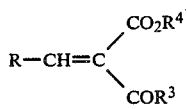 (VI)

in which
R, $R^3$ and $R^4$ have the abovementioned meaning, but $R^3$ does not represent an amino or hydroxymethyl group,
with amidinoacetates of the general formula (XI)

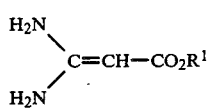 (XI)

in which $R^1$ has the abovementioned meaning, optionally in the presence of inert organic solvents or (H) in the case where X in the general formula (I) represents N-$R^5$, wherein $R^5$ has the abovementioned meaning, and $R^2$ or $R^3$ represent the hydroxymethyl group, the compounds according to the invention are preferably prepared by subjecting the corresponding compounds according to the invention, in which $R^2$ or $R^3$ denote acetoxymethyl, to the conditions of acid or basic hydrolysis, the acetoxymethyl group being converted into a hydroxymethyl group or (I) in the case where X in the general formula (I) represents an oxygen atom and $R^2$ or $R^3$ represents an amino group, the compounds according to the invention are preferably prepared by 1. reacting ylidene- β-ketoesters of the general formula (II)

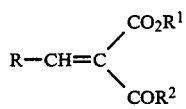
(II)

in which

R, $R^1$ and $R^2$ have the abovementioned meaning, but $R^2$ does not represent the amino or hydroxymethyl group, with cyanoacetates of the general formula (XII)

$N\equiv C-CH_2-CO_2R^4$ (XII)

in which, $R^4$ has the abovementioned meaning, optionally in the presence of organic solvents, or 2. reacting ylidene- β-ketoesters of the general formula (VI)

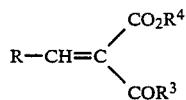
(VI)

in which

R, $R^4$ and $R^3$ have the abovementioned meaning, but $R^3$ does not represent the amino or hydroxymethyl group, with cyanoacetates of the general formula (XIII)

$N\equiv C-CH_2-CO_2R^1$ (XIII)

in which, $R^1$ has the abovementioned meaning, optionally in the presence of organic solvents.

The compounds according to the invention have valuable pharmacological properties. In particular, due to their unexpectedly lasting circulatory effect, they can find use as antihypertensive agents, as vasodilators, as cerebral therapeutic agents and as coronary therapeutic agents and are thus regarded as beneficial to pharmacy.

The lasting action on the blood pressure is of particular interest.

Depending on the type of starting materials used, the synthetic variants for the compounds according to the invention can be represented by the following reaction schemes:

(A)
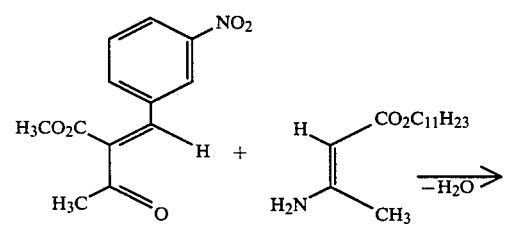

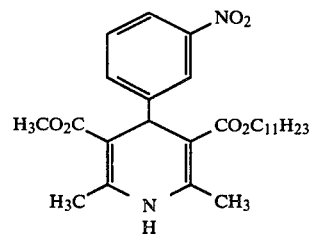

(B)
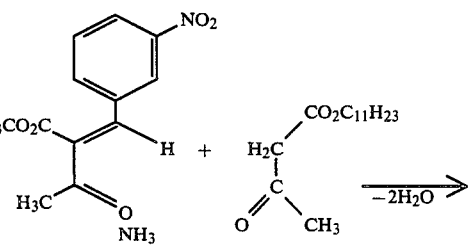

(C)
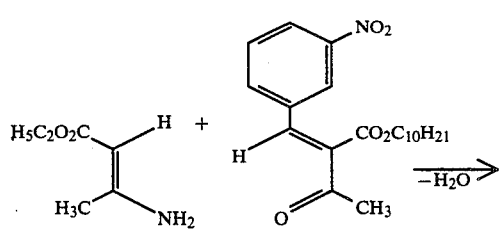

(D)
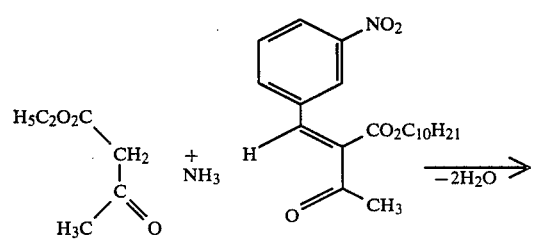

-continued

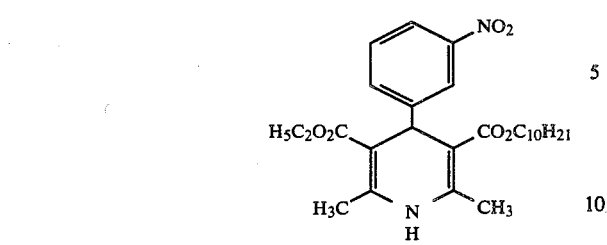
(E)

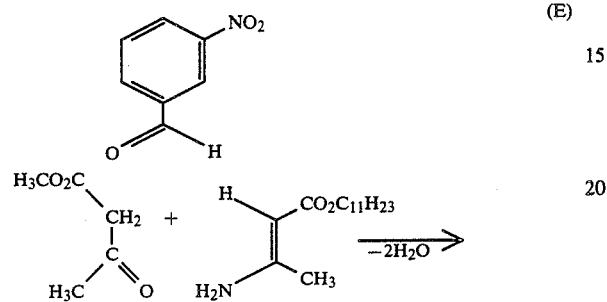

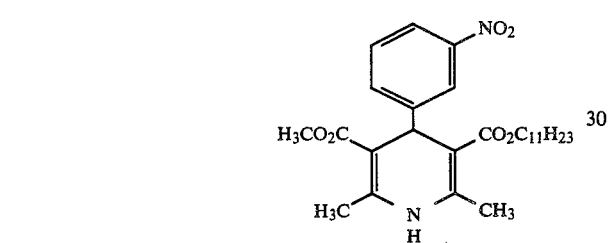
(F)

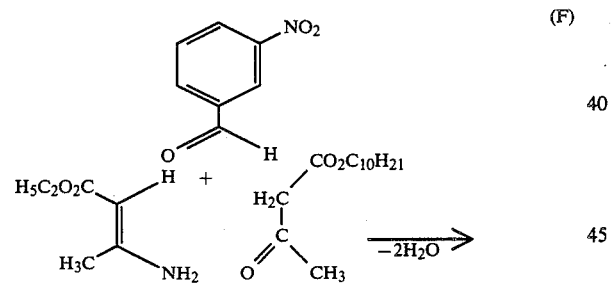

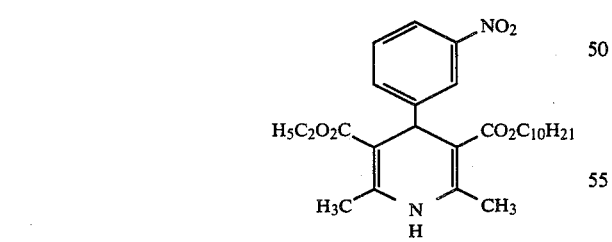
(G)

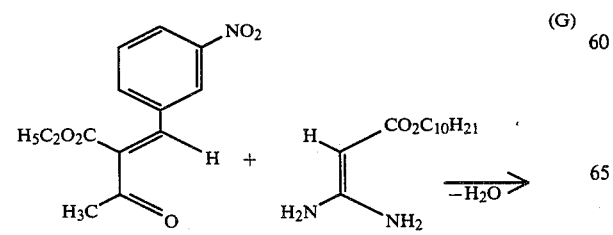

-continued

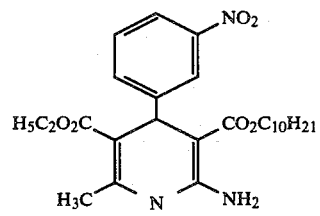
(H)

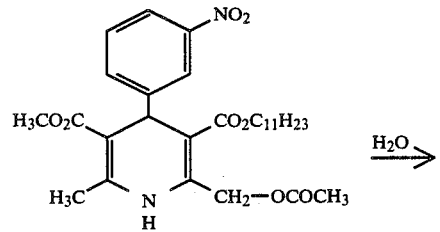

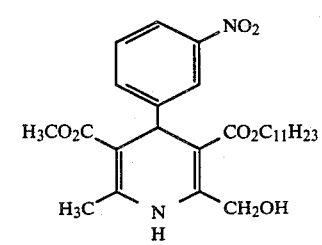
(I)

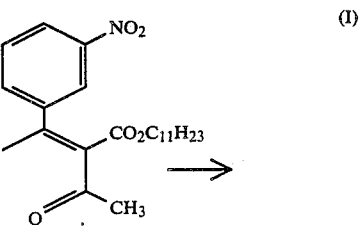

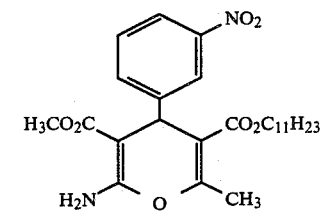

The compounds of particular interest according to the invention are those of the general formula (I)

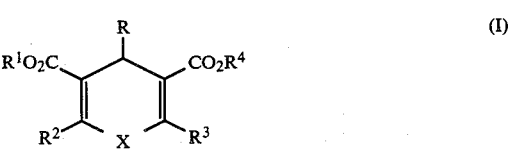
(I)

in which

R represents phenyl, naphthyl or thienyl, furyl, pyrryl, pyrazoly, imidazolyl, oxazolyl, isoxazolyl, thiazolyl, pyridyl, pyridazinyl, pyrimidyl, pyrazinyl, indolyl, benzimidazolyl, benzoxazolyl, benzisoxazolyl, benzoxadiazolyl, quinolyl, isoquinolyl, quinazolyl or quinoxalyl, it being possible for the ring systems mentioned each to be substituted by 1 or 2 identical or different substituents from the group comprising phenyl, straight-chain or branched alkyl having 1 to 8 carbon atoms, cycloalkyl having 3 to 7 carbon atoms, alkoxy having 1 to 4 carbon atoms, trimethylene, tetramethylene and pentamethylene, dioxymethylene, halogen, trifluoromethyl, trifluoromethoxy, difluoromethoxy, tetrafluoroethoxy, nitro, cyano, azido or $SO_m$-alkyl, wherein m denotes a number from 0 to 2 and alkyl preferably contains 1 to 4 carbon atoms, $R^1$ represents a straight-chain, branched or cyclic, saturated or unsaturated hydrocarbon radical having up to 20 carbon atoms, which is optionally interrupted by 1 oxygen atom in the chain and/or is optionally substituted by halogen, cyano, hydroxyl, acetoxy, phenyl, phenoxy or an amino group, which in turn is optionally substituted by 2 identical or different substituents from the group comprising alkyl having 1 to 4 carbon atoms, phenyl or benzyl, $R^4$ represents a straight-chain, branched or cyclic, saturated or unsaturated aliphatic hydrocarbon radical having 7 to 14 carbon atoms, which is optionally interrupted by an oxygen atom in the chain and/or is optionally substituted by halogen, hydroxyl or acetoxy, $R^2$ and $R^3$ are identical or different and each represent hydrogen, a straight-chain or branched alkyl radical having up to 4 carbon atoms, a phenyl radical or a benzyl radical, or one of the substituents $R^2$ or $R^3$ represents a hydroxymethyl, acetoxymethyl or amino group, the other substituent having the abovementioned meaning, and X represents N-$R^5$, wherein $R^5$ represents hydrogen, a straight-chain or branched alkyl radical, which is optionally interrupted by an oxygen atom, having up to 4 carbon atoms, a morpholinoethyl radical, a phenyl radical or a benzyl radical, or X represents an oxygen atom, in which case one of the substituents $R^2$ or $R^3$ then always denotes an amino group.

Compounds of the general formula (I) which may be preferably mentioned are those in which R represents phenyl, pyridyl, thienyl or furyl, the phenyl ring optionally being substituted by one or two identical or different substituents from the group comprising phenyl, alkyl having 1 to 4 carbon atoms, alkoxy having 1 to 2 carbon atoms, fluorine, chlorine, bromine, trifluoromethyl, trifluoromethoxy, difluoromethoxy, nitro, cyano, azido or alkylmercapto having 1 to 4 carbon atoms in the alkyl radical, $R^1$ represents a straight-chain, branched or cyclic, saturated or unsaturated hydrocarbon radical having up to 14 carbon atoms, which is optionally interrupted by an oxygen atom and/or is optionally substituted by fluorine, chlorine, cyano, hydroxyl or amino, $R^4$ represents a straight-chain, branched or cyclic, saturated or unsaturated aliphatic hydrocarbon radical having 7 to 12 carbon atoms, which is optionally interrupted by an oxygen atom in the chain and/or is optionally substituted by fluorine, chlorine, hydroxyl or acetoxy, $R^2$ and $R^3$ are identical or different and each represent hydrogen, alkyl having 1 to 2 carbon atoms, phenyl or benzyl or one of the substituents $R^2$ or $R^3$ represents a hydroxymethyl, acetoxymethyl or amino group, the other substituent having the previously mentioned meaning, X represents N-$R^5$, wherein $R^5$ represents hydrogen, an alkyl radical having up to 4 carbon atoms, which is optionally interrupted by an oxygen atom, a morpholinoalkyl radical having 1 to 4 carbon atoms in the alkyl moiety, a phenyl radical or a benzyl radical or X represents an oxygen atom, in which case one of the substituents $R^2$ or $R^3$ then always denotes an amino group.

Compounds of the general formula (I) which may be very particularly emphasized are those in which R represents a phenyl radical which contains one or two identical or different substituents from the group comprising chlorine, trifluoromethyl, nitro or cyano or R represents a benzoxadiazolyl radical, $R^1$ represents a straight-chain or branched hydrocarbon radical having up to 7 carbon atoms, which is optionally interrupted by an oxygen atom in the chain and/or is optionally substituted by fluorine or chlorine or an amino group, which in turn is optionally substituted by two methyl groups or by a methyl and a benzyl group, $R^4$ denotes a straight-chain, branched or cyclic, saturated or unsaturated aliphatic hydrocarbon radical having seven to twelve carbon atoms, which is optionally interrupted by an oxygen atom in the chain or is optionally substituted by fluorine, chlorine or hydroxyl, $R^2$ and $R^3$ each represent hydrogen or an alkyl radical having 1 to 2 carbon atoms, or one of the substituents $R^2$ or $R^3$ represents the amino group, in which case the other substituent has the abovementioned meaning, and X represents N-$R^5$, wherein $R^5$ represents a hydrogen atom or an alkyl radical having up to 3 carbon atoms, or X represents an oxygen atom, in which case one of the substituents $R^2$ or $R^3$ always represents an amino group.

Process variant A

In accordance with process A, an ylidene- β-ketoester of the general formula II

is reacted with an enaminocarboxylate of the general formula III

The ylidene- β-ketoesters of the general formula (II) used as starting materials are known from the literature or can be prepared by methods known from the literature (cf. for example G. Jones "The Knoevenagel Condensation" in Org. Reactions, Vol. XV, 204 et seq. (1969)).

Examples which may be mentioned are:
methyl benzylideneformylacetate,
methyl benzylideneacetoacetate,
ethyl 2'-nitrobenzylideneacetoacetate,
n-butyl 3'-nitrobenzylideneacetoacetate,
decyl 3'-nitrobenzylideneacetoacetate,
dodecyl 3'-nitrobenzylideneacetoacetate,
tetradecyl 3'-nitrobenzylideneacetoacetate, ethyl 2′,3′-dichlorobenzylideneacetoacetate,
decyl 2′,3′-dichlorobenzylideneacetoacetate,
hexadecyl 2′-chlorobenzylideneacetoacetate,
2-propoxyethyl 3′-chlorobenzylideneacetoacetate,
2-chloroethyl 3-cyanobenzylideneacetoacetate,
2,2,2-trifluoroethyl 2′-chlorobenzylideneacetoacetate,
2-cyanoethyl 2′-trifluoromethylbenzylideneacetoacetate,
2-acetoxyethyl 2′-difluoromethoxybenzylideneacetoacetate,
2-phenoxyethyl 3-methylsulphonylbenzylideneacetoacetate,
2-N-benzyl-N-methyl-aminoethyl 3′-nitrobenzylideneacetoacetate,
isopropyl 3′-nitrobenzylidenepropionylacetate,
cyclopentyl 2′-nitrobenzylideneacetoacetate,
isobutyl 2′-nitrobenzylideneacetoacetate,
neopentyl 3′-nitrobenzylideneacetoacetate,
allyl 3′-nitrobenzylideneacetoacetate,
ethyl α-acetyl- β-(3-pyridyl)acrylate,
octyl α-acetyl- β-(3-pyridyl)acrylate,
decyl α-acetyl- β-(3-pyridyl)acrylate,
tetradecyl α-acetyl- β-(3-pyridyl)acrylate, and
ethyl α-acetyl- β-(4-benzoxadiazolyl)acrylate.

The enaminocarboxylates of the general formula (III) used as starting materials are known from the literature or can be prepared by methods known from the literature (cf. A. C. Cope, J. Amer. chem. Soc. 67, 1017 (1945)).

Examples which may be mentioned are:
heptyl β-aminocrotonate,
octyl β-aminocrotonate,
nonyl β-aminocrotonate,
decyl β-aminocrotonate,
undecyl β-aminocrotonate,
dodecyl β-aminocrotonate,
tetradecyl β-aminocrotonate,
2-pentyloxyethyl β-aminocrotonate,
2-hexyloxyethyl β-aminocrotonate,
heptyl β-aminocrotonate,
octenyl β-aminocrotonate,
ω-chloroheptyl β-aminocrotonate,
ω-chlorodecyl β-aminocrotonate,
ω-hydroxydecyl β-aminocrotonate,
ω-acetoxydecyl β-aminocrotonate,
ω-hydroxyundecyl β-aminocrotonate,
ω-acetoxyundecyl β-aminocrotonate,
decyl β-methylaminocrotonate,
decyl β-benzylaminocrotonate,
decyl β-amino-β-ethyl-acrylate,
decyl β-amino-β-propyl-acrylate,
decyl β-amino-β-benzyl acrylate,
decyl β-amino-β-acetoxymethyl-acrylate,
undecyl β-amino-β-acetoxymethyl-acrylate.

Suitable diluents are all inert organic solvents. These include, preferably, alcohols, such as ethanol, methanol, isopropanol, ethers, such as dioxane, diethyl ether, tetrahydrofuran, glycol monomethyl ether, glycol dimethyl ether or glacial acetic acid, dimethylformamide, dimethyl sulphoxide, acetonitrile, pyridine and hexamethylphosphoric triamide.

The reaction temperatures can be varied within a wide range. In general, the reaction is carried out between 20° and 150° C., preferably between 20° and 100° C., in particular at the boiling point of the particular solvent.

The reaction can be carried out under normal pressure, but also under elevated pressure. In general, it is carried out under normal pressure.

In carrying out the process according to the invention, one mol of the ylidene-β-ketoester of the formula (II) is reacted with one mol of enaminocarboxylate of the formula (III) in a suitable solvent. The isolation and purification of the substances according to the invention are preferably carried out such that the solvent is distilled off in vacuo and the residue, which is, in some cases, only obtained crystalline after cooling in ice, is recrystallized from a suitable solvent.

Process variant B

According to process B, an ylidene-β-ketoester of the general formula II

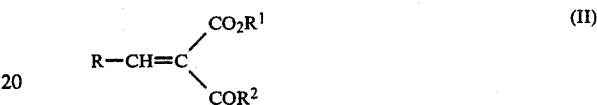

is reacted with an amine of the general formula (IV) and a β-ketocarboxylate of the general formula (V)

Examples of the ylidene-β-ketoesters of the general formula II used as starting substances have already been listed under process variant A.

The amines of the formula (IV) which can be used according to the invention are already known Examples which may be mentioned are: ammonia, methylamine, n-propylamine, isopropylamine, butylamine β-methoxyethylamine, benzylamine and 2-(N-morpholinyl)ethylamine.

The β-ketocarboxylates of the general formula (V) used as starting materials are known from the literature or can be prepared by methods known from the literature (for example D Borrmann, "Umsetzung von Diketen mit Alkoholen, Phenolen und Mercaptanen" [Reaction of diketene with alcohols, phenols and mercaptans] in Houben-Weyl, Methoden der Organischen Chemie [Methods of Organic Chemistry], Volume VII/4, 230 et seq. (1968); Y. Oikawa, K. Sugano and O. Yonemitsu, J. Org. Chem 43, 2087 (1978)).

Examples which may be mentioned are:
heptyl acetoacetate,
nonyl acetoacetate,
decyl acetoacetate,
undecyl acetoacetate,
tetradecyl acetoacetate,
2-pentyloxyethyl acetoacetate,
heptenyl acetoacetate,
ω-chloroheptyl acetoacetate,
ω-hydroxydecyl acetoacetate,
ω-acetoxyundecyl acetoacetate,
decyl propionylacetate and
decyl butyrylacetate.

Suitable diluents are all inert organic solvents. These preferably include alcohols, such as ethanol, methanol, isopropanol, ethers, such as dioxane, diethyl ether, tetrahydrofuran, glycol monomethyl ether, glycol dimethyl ether or glacial acetic acid, dimethylformamide, dimethyl sulphoxide, acetonitrile, pyridine and hexamethylphosphoric triamide.

The reaction temperatures can be varied within a wide range. In general, the reaction is carried out between 20° and 150° C., but preferably at the boiling point of the particular solvent.

The reaction can be carried out under normal pressure and also under elevated pressure. In general, it is carried out under normal pressure.

In carrying out the process according to the invention, the materials of the formulae (II), (IV) and (V) involved in the reaction are each employed in molar amounts. The amine used is advantageously added in an excess of 1 to 2 mols. The compounds according to the invention can easily be purified by recrystallisation from a suitable solvent.

Process variant C

According to process C, an ylidene-β-ketoester of the general formula (VI)

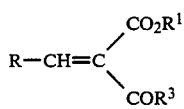 (VI)

is reacted with an enaminocarboxylate of the general formula (VII)

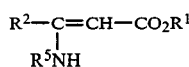 (VII)

The ylidene-β-ketoesters of the formula (VI) used as starting materials are known from the literature or can be prepared by methods known from the literature (cf. for example, G. Jones "The Knoevenagel Condensation" in Org. Reactions, Vol. XV, 204 et seq. (1967)).

Examples which may be mentioned are:
heptyl benzylideneacetoacetate,
heptyl 3'-nitrobenzylideneacetoacetate,
octyl 2-chlorobenzylideneacetoacetate,
nonyl 2-cyanobenzylideneacetoacetate,
decyl 3-nitrobenzylideneacetoacetate,
decyl 2-trifluoromethylbenzylideneacetoacetate,
decyl 2 3-dichlorobenzylideneacetoacetate,
undecyl 3-nitrobenzylideneacetoacetate,
dodecyl 3-nitrobenzylideneacetoacetate,
tetradecyl 3-nitrobenzylideneacetoacetate,
2-pentoxyethyl 2-nitrobenzylideneacetoacetate,
ω-chlorodecyl 3-nitrobenzylideneacetoacetate,
ω-hydroxydecyl 3-nitrobenzylideneacetoacetate,
ω-acetoxydecyl 3-nitrobenzylideneacetoacetate,
decyl α-acetyl-β-(3-pyridyl)acrylate,
decyl α-acetyl-β-(2-pyridyl)acrylate,
decyl α-propionyl-β-(3-pyridyl)acrylate,
decyl α-acetyl-β-(4-benzoxadiazolyl)acrylate and
decyl α-acetyl-β-(2-methylthio-3-pyridyl)acrylate.

The enaminocarboxylates of the formula (VII) used as starting materials are known from the literature or can be prepared by methods known from the literature (cf. A. C. Cope, J. Amer. Chem. Soc. 67, 1017 (1945)).

Examples which may be mentioned are:
hexyl β-aminocrotonate,
octyl β-aminocrotonate,
decyl β-aminocrotonate,
tetradecyl β-aminocrotonate,
isopropyl β-aminocrotonate,
cyclopentyl β-aminocrotonate,
benzyl β-aminocrotonate,
allyl β-aminocrotonate,
2-methoxyethyl β-aminocrotonate,
2-propoxyethyl β-aminocrotonate,
2,2,2-trifluoroethyl β-aminocrotonate,
2-chloroethyl β-aminocrotonate,
2-cyanoethyl β-aminocrotonate,
2-hydroxyethyl β-aminocrotonate,
2-acetoxyethyl β-aminocrotonate,
2-phenylethyl β-aminocrotonate,
2-phenoxyethyl β-aminocrotonate,
2-dimethylaminoethyl β-aminocrotonate,
2-N-benzyl-N-methylaminoethyl β-aminocrotonate,
ethyl β-methylaminocrotonate,
ethyl β-butylaminocrotonate and
ethyl β-benzylaminocrotonate.

Suitable diluents are all inert organic solvents These preferably include alcohols, such as ethanol, methanol, isopropanol, ethers, such as dioxane, diethyl ether, tetrahydrofuran, glycol monomethyl ether, glycol dimethyl ether or glacial acetic acid, dimethylformamide, dimethyl sulphoxide, acetonitrile, pyridine and hexamethylphosphoric triamide.

The reaction temperatures can be varied within a wide range. In general the reaction is carried out between 20° and 150° C., preferably between 20° and 100° C., in particular at the boiling point of the particular solvent.

The reaction can be carried out under normal pressure and also under elevated pressure. In general, it is carried out under normal pressure.

In carrying out the process according to the invention, one mol of the ylidene-β-ketoester of the formula (VI) is reacted with one mol of enaminocarboxylate of the formula (VII) in a suitable solvent.

Process variant D

According to process D, an ylidene-β-ketoester of the general formula (VI)

 (VI)

is reacted with an amine of the formula (IV) and a β-ketocarboxylate of the general formula (VIII)

 (IV)

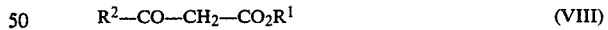 (VIII)

Examples of the ylidene-β-ketoesters of the formula (VI) used as starting compounds have already been listed under process variant C.

The amines of the formula (IV) which can be used according to the invention have already been described under process variant B.

The β-ketocarboxylates of the formula (VIII) used as starting materials are known from the literature or can be prepared by methods known from the literature (for example D. Borrmann, "Umsetzung von Diketen mit Alkoholen, Phenolen und Mercaptanen" [Reaction of diketene with alcohols, phenols and mercaptans] in Houben-Weyl, Methoden der Organischen Chemie [Methods of Organic Chemistry], Volume VII/4, 230 et seq. (1968); Y. Oikawa, K. Sugano a O. Yonemitsu, J. Org. Chem. 43, 2087 (1978)).

Examples which may be mentioned are:

methyl acetoacetate,
ethyl acetoacetate,
hexyl acetoacetate,
octyl acetoacetate,
decyl acetoacetate,
tetradecyl acetoacetate,
isopropyl acetoacetate,
neopentyl acetoacetate,
cyclopentyl acetoacetate,
allyl acetoacetate,
2-methoxyethyl acetoacetate,
2,2,2-trifluoroethyl acetoacetate,
2-chloroethyl acetoacetate,
2-cyanoethyl acetoacetate,
2-acetoxyethyl acetoacetate,
benzyl acetoacetate,
2-phenylethyl acetoacetate,
2-phenoxyethyl acetoacetate,
2-dimethylaminoethyl acetoacetate,
2-N-benzyl-N-methylaminoethyl acetoacetate,
ethyl propionylacetate and
decyl propionylacetate.

Suitable diluents are all inert organic solvents. These preferably include alcohols, such as ethanol, methanol, isopropanol, ethers, such as dioxane, diethyl ether, tetrahydrofuran, glycol monomethyl ether, glycol dimethyl ether or glacial acetic acid, dimethylformamide, dimethyl sulphoxide, acetonitrile, pyridine and hexamethylphosphoric triamide.

The reaction temperatures can be varied within a wide range. In general, the reaction is carried out between 20° and 150° C., in particular between 40° and 120° C., but preferably at the boiling point of the particular solvent.

The reaction can be carried out under normal pressure and also under elevated pressure. In general, it is carried out under normal pressure.

In carrying out the process according to the invention, the materials of the formula (VI), (IV) and (VIII) involved in the reaction are each employed in molar amounts. The amine used is advantageously added in an excess of 1 to 2 mols.

Process variants E and F

According to processes E and F, an aldehyde of the formula (IX)

(IX)

is reacted either (process E) with an enaminocarboxylate of the formula (III) and a

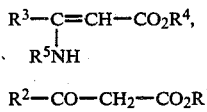
(III)

$$R^2—CO—CH_2—CO_2R^1 \qquad (VIII)$$

β-ketocarboxylate of the general formula (VIII) or (process F) with an enaminocarboxylate of the general formula (VII)

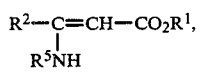
(VII)

$$R^3—CO—CH_2—CO_2R^4 \qquad (V)$$

and a β-ketocarboxylate of the general formula (V).

The enaminocarboxylates of the general formula (III) and (VII) which can be used according to the invention have already been mentioned under process variants A and C. The β-ketocarboxylates of the general formulae (VIII) and (V) which can be employed according to the invention have already been described under process variants D and B.

The aldehydes of the formula (IX) used as starting materials are known from the literature or can be prepared by methods known from the literature (cf. for example, E. Mosettig, Org. Reactions VIII, 218 et seq. (1954)).

Examples which may be mentioned are: benzaldehyde, 2-, 3- or 4-phenylbenzaldehyde, α- or β-naphthylaldehyde, 2-, 3- or 4-methylbenzaldehyde, 2- or 4-n-butylbenzaldehyde, 2-, 3- or 4-isopropylbenzaldehyde, 2- or 4-cyclopropylbenzaldehyde, 2,3-tetramethylenebenzaldehyde, 3,4-dioxymethylenebenzaldehyde, 2-, 3- or 4-methoxybenzaldehyde, 2-cyclopropylmethoxybenzaldehyde, 2-, 3- or 4-chloro/bromo/-fluorobenzaldehyde, 2-, 3- or 4-trifluoromethylbenzaldehyde, 2-, 3- or 4-trifluoromethoxybenzaldehyde, 2-, 3- or 4-difluoromethoxybenzaldehyde, 2-, 3- or 4-nitrobenzaldehyde, 2-, 3- or 4-cyanobenzaldehyde, 3-azidobenzaldehyde, 2-, 3- or 4-methylthiobenzaldehyde, 2-, 3- or 4-methylsulphinylbenzaldehyde, 2-, 3-or 4-methylsulphonylbenzaldehyde, 2,3-, 2,4- or 2,6-dichlorobenzaldehyde, 2-fluoro-3-chlorobenzaldehyde, 2,4-dimethylbenzaldehyde, 2,4- or 2,6-dinitrobenzaldehyde, 2-chloro-6-nitrobenzaldehyde, 4-chloro-2-nitrobenzaldehyde, 2-nitro-4-methoxybenzaldehyde, 2-nitro-4-cyanobenzaldehyde, 2-chloro-4-cyanobenzaldehyde, 4-cyano-2-methylbenzaldehyde, 3-methyl-4-trifluoromethylbenzaldehyde, 3-chloro-2-trifluoromethylbenzaldehyde, thiophene-2-aldehyde, furan-2-aldehyde, pyrrole-2-aldehyde, pyrazole-4-aldehyde, imidazole-2-aldehyde, oxazole-2-aldehyde, isoxazole-3-aldehyde, thiazole-2-aldehyde, pyridine-2-, 3- or 4-aldehyde, 6-methylpyridine-2-aldehyde, 2-methylthiopyridine-3-aldehyde, indole-3-aldehyde, benzimidazole-2-aldehyde, benzoxazole-4-aldehyde, benzoxadiazole-4-aldehyde, quinoline-4-aldehyde, quinazoline-2-aldehyde, and quinoxaline-5-aldehyde.

Suitable diluents are all inert organic solvents. These preferably include alcohols, such as ethanol, methanol, isopropanol, ethers, such as dioxane, diethyl ether, tetrahydrofuran, glycol monomethyl ether, glycol dimethyl ether or glacial acetic acid, dimethylformamide, dimethyl sulphoxide, acetonitrile, pyridine and hexamethylphosphoric triamide.

The reaction temperatures can be varied within a wide range. In general, the reaction is carried out between 20° and 150° C., but preferably at the boiling point of the particular solvent.

The reaction can be carried out under normal pressure, and also under elevated pressure. In general, it is carried out under normal pressure.

In carrying out the process according to the invention, the materials involved in the reaction are each employed in molar amounts.

Process variant G

In the case where X in the general formula I denotes NH and $R^2$ or $R^3$ represent an amino group, it has been found that the compounds according to the invention are obtained by either reacting ylidene-β-ketoesters of the general formula (II)

$$R-CH=C\begin{array}{c}CO_2R^1\\ \\COR^2\end{array} \quad (II)$$

$$\begin{array}{c}H_2N\\ \\H_2N\end{array}C=CH-CO_2R^4 \quad (X)$$

with amidinoacetates of the general formula (X) or reacting ylidene-β-ketoesters of the general formula (VI)

$$R-CH=C\begin{array}{c}CO_2R^4\\ \\COR^3\end{array}, \begin{array}{c}H_2N\\ \\H_2N\end{array}C=CH-CO_2R^1$$

(VI)      (XI)

with amidinoacetates of the general formula (XI).

The ylidene-β-ketoesters of the general formulae (II) and (VI) which can be used according to the invention have already been described under process variant A and C.

The amidinoacetates of the formula (X) used as starting substances are new, but can be prepared by methods known from the literature (cf. for example, H. Meyer, F. Bossert and H. Horstmann, Liebigs Ann. Chem. 1977, 1895).

Examples which may be mentioned are:
heptyl amidinoacetate,
octyl amidinoacetate,
decyl amidinoacetate,
undecyl amidinoacetate,
dodecyl amidinoacetate,
tetradecyl amidinoacetate,
2-pentoxyethyl amidinoacetate,
2-heptyloxyethyl amidinoacetate,
ω-chlorodecyl amidinoacetate and
ω-acetoxydecyl amidinoacetate.

The amidinoacetates of the formula (XI) used as starting substances are known from the literature or can be prepared by known methods (cf. for example, H. Meyer, F. Bossert and H. Horstmann, Liebigs Ann. Chem. 1977, 1895).

Examples which may be mentioned are:
decyl amidinoacetate,
tetradecyl amidinoacetate,
2-methoxyethyl amidinoacetate,
2-propoxyethyl amidinoacetate,
2-chloroethyl amidinoacetate,
benzyl amidinoacetate,
2-phenoxyethyl amidinoacetate,
2-dimethylaminoethyl amidinoacetate,
2-N-benzyl-N-methylaminoethyl amidinoacetate,
isopropyl amidinoacetate and
cyclopentyl amidinoacetate.

The amidines can be employed either in free form or in the form of their salts (for example hydrohalides). They are liberated from the salts with basic agents (for example alkali metal alcoholates).

Suitable diluents are all inert organic solvents. These preferably include alcohols, such as methanol, ethanol, propanol; ethers, such as dioxane, diethyl ether or glacial acetic acid, pyridine, dimethylformamide, dimethyl sulphoxide or acetonitrile.

The reaction temperatures can be varied within a wide range. In general, the reaction is carried out between 20° and 250° C., preferably at the boiling point of the solvent.

The reaction can be carried out under normal pressure, and also under elevated pressure. In general, it is carried out under normal pressure.

In carrying out the process according to the invention, the substances involved in the reaction are each employed in molar amounts.

Process variant H

In the case where X in the general formula (I) represents N-R$^5$, wherein R$^5$ has the abovementioned meaning, and R$^2$ or R$^3$ represent the hydroxymethyl group, it has proved to be advantageous to subject the appropriate compounds according to the invention, in which R$^2$ or R$^3$ represents acetoxymethyl, to the conditions of acid or basic hydrolysis.

Suitable acids are primarily hydrohalic acids, acetic acid or ammonium chloride, and alkali metal and alkaline earth metal carbonates have been found to be advantageous as bases.

Suitable diluents are water and all inert organic solvents which are miscible with water. These preferably include alcohols, such as methanol or ethanol, ethers, such as tetrahydrofuran or ethylene glycol dimethyl ether, glacial acetic acid, pyridine, dimethylformamide, dimethyl sulphoxide or acetonitrile.

The reaction temperatures can be varied within a wide range. In general, the reaction is carried out between 0° and 100° C., preferably at room temperature.

Process variant I

In the case where X in the general formula (I) represents an oxygen atom and R$^2$ or R$^3$ represent an amino group, it has been found that the compounds according to the invention are obtained by either reacting ylidene-β-ketoesters of the general formula (II)

$$R-CH=C\begin{array}{c}CO_2R^1\\ \\COR^2\end{array}, N\equiv C-CH_2-CO_2R^4$$

(II)      (XII)

with cyanoacetates of the general formula (XII) or reacting ylidene-β-ketoesters of the general formula (VI)

$$R-CH=C\begin{array}{c}CO_2R^4\\ \\COR^3\end{array}, N\equiv C-CH_2-CO_2R^1$$

(VI)      (XIII)

with cyanoacetates of the general formula (XIII).

The ylidene-β-ketoesters of the general formulae (II) and (VI) which can be used according to the invention have already been described under process variant A and C.

The cyanoacetates of the formulae (XII) and (XIII) used as starting substances are known or can be prepared by methods known from the literature (see Org. Syntheses, Collect. Vol. I, p. 254 (1958)).

Examples which may be mentioned are:
ethyl cyanoacetate,
butyl cyanoacetate,
heptyl cyanoacetate,
decyl cyanoacetate,
undecyl cyanoacetate,
tetradecyl cyanoacetate,
isopropyl cyanoacetate,
cyclopentyl cyanoacetate,
benzyl cyanoacetate,
2-methoxyethyl cyanoacetate,
2-propoxyethyl cyanoacetate,
2-pentyloxyethyl cyanoacetate,
2-phenoxyethyl cyanoacetate,
2,2,2-trifluoroethyl cyanoacetate,
2-acetoxyethyl cyanoacetate,
2-dimethylaminoethyl cyanoacetate and
2-N-benzyl-N-methylaminoethyl cyanoacetate.

The reaction is preferably carried out in the presence of basic catalysts, such as, for example, piperidine.

Suitable diluents are all inert organic solvents. These preferably include alcohols, such as ethanol, methanol, isopropanol, ethers, such as dioxane, diethyl ether, tetrahydrofuran, glycol monomethyl ether, glycol dimethyl ether, dimethylformamide, dimethyl sulphoxide, acetonitrile, pyridine and hexamethylphosphoric triamide.

The reaction temperature can be varied within a wide range. In general, the reaction is carried out between 20° and 150° C., but preferably at the boiling point of the particular solvent.

The reaction can be carried out under normal pressure, and also under elevated pressure. In general, it is carried out under normal pressure.

In carrying out the process according to the invention, the substances involved in the reaction are each employed in molar amounts in the presence of a basic catalyst.

The foregoing preparation processes are only mentioned for the purposes of elucidation, and the preparation of the compounds of the formula (I) is not restricted to these processes, but every modification of these processes can be used in the same manner for the preparation of the compounds according to the invention.

Depending on the choice of starting substances, the compounds according to the invention can exist in stereoisomeric forms, which are related either as image and mirror image (enantiomers) or which are not related as image and mirror image (diastereomers). The present invention relates not only to the antipodes, but also to the racemic forms and also to the mixtures of diastereomers. The racemic forms can be separated, as can the diastereomers, in a known manner into the stereoisomerically homogeneous constituents (cf. for example, E. L. Eliel, Stereochemistry of Carbon Compounds, McGraw Hill, 1962).

Apart from the preparation examples listed below, the following active compounds according to the invention may be mentioned:
heptyl methyl 1,4-dihydro-2,6-dimethyl-4-(2-nitrophenyl)pyridine-3,5-dicarboxylate,
decyl ethyl 1,4-dihydro-2,6-dimethyl-4-(2-nitrophenyl)-pyridine-3,5-dicarboxylate,
methyl undecyl 1,4-dihydro-2,6-dimethyl-4-(2-nitrophenyl)pyridine-3,5-dicarboxylate,
heptyl tetradecyl 1,4-dihydro-2,6-dimethyl-4-(2-nitrophenyl)pyridine-3,5-dicarboxylate,
decyl 2,2,2-trifluoroethyl 1,4-dihydro-2,6-dimethyl-4-(2-nitrophenyl)pyridine-3,5-dicarboxylate,
3-decyl 5-ethyl 2-amino-1,4-dihydro-6-methyl-4-(2-nitrophenyl)pyridine-3,5-dicarboxylate,
ethyl heptyl 1,4-dihydro-2,6-dimethyl-4-(3-nitrophenyl)pyridine-3,5-dicarboxylate,
decyl 2,2,2-trifluoroethyl 1,4-dihydro-2,6-dimethyl-4-(3-nitrophenyl)pyridine-3,5-dicarboxylate,
2-N-benzyl-N-methylaminoethyl decyl 1,4-dihydro-2,6-dimethyl-4-(3-nitrophenyl)pyridine-3,5-dicarboxylate,
2-decyl 5-ethyl 1,4-dihydro-2-hydroxymethyl-6-methyl-4-(3-nitrophenyl)pyridine-3,5-dicarboxylate,
decyl ethyl 1,4-dihydro-2,6-dimethyl-4-(3-pyridyl)pyridine-3,5-dicarboxylate,
decyl ethyl 1,4-dihydro-2,6-dimethyl-4-(2,1,3-benzoxadiazol-4-yl)pyridine-3,5-dicarboxylate,
decyl ethyl 1,4-dihydro-2,6-dimethyl-4-(2-cyanophenyl)pyridine-3,5-dicarboxylate,
decyl ethyl 1,4-dihydro-2,6-dimethyl-4-(2-trifluoromethoxyphenyl)pyridine-3,5-dicarboxylate,
decyl ethyl 1,4-dihydro-2,6-dimethyl-4-(2-methoxyphenyl)pyridine-3,5-dicarboxylate,
decyl ethyl 1,4-dihydro-2,6-dimethyl-4-(2,3-dichlorophenyl)pyridine-3,5-dicarboxylate,
decyl 2,2,2-trifluoroethyl 1,4-dihydro-2,6-dimethyl-4-(2,3-dichlorophenyl)pyridine-3,5-dicarboxylate,
methyl undecyl 1,4-dihydro-2,6-dimethyl-4-(2-trifluoromethylphenyl)pyridine-3,5-dicarboxylate, The new compounds have a wide and diverse spectrum of pharmacological activity with a surprisingly long duration of activity.

In an animal experiment the following major effects could be demonstrated in particular:

1. The compounds, on parenteral, oral and perlingual administration, bring about a marked and lasting dilation of the coronary vessels. This effect on the coronary vessels is reinforced by a simultaneous relieving effect on the heart resembling that of nitrites. They affect or change the cardiac metabolism in the direction of a saving of energy.

2. The excitability of the pace-setting and stimulus-conduction system within the heart is decreased, so that a detectable anti-fibrillatory effect results at therapeutic doses.

3. The tone of the smooth muscle of the vessels is greatly decreased under the action of the compounds. This vasospasmolytic effect can take place in the entire vascular system or can manifest itself, in a more or less isolated fashion, in restricted vascular zones (such as, for example, in the central nervous system). The compounds are therefore particularly suitable as cerebral therapeutic agents.

4. The compounds decrease the blood pressure of normotensive and hypertensive animals and can thus be used as antihypertensive agents.

5. Compounds have strong muscular-spasmolytic effects, which become evident on the smooth muscle of the stomach, intestinal tract, urogenital tract and the respiratory system.

6. The advantage of the compounds according to the invention is their long-lasting hypotensive action. Thus the compound according to Example 1 has a hypotensive effect lasting about 24 hours on the hypertensive rat. A similar increase in the duration of action can be shown in hypertensive dogs. An additional advantage for therapeutic use is the mild onset of action of the compounds according to the invention. 2-4 hours pass in the dog and 4-6 hours in the rat until the maximum effect is reached.

Because of these properties, the compounds according to the invention are particularly suitable for the prophylaxis and therapy of chronic and acute ischaemic heart disease in the widest sense, for the therapy of high blood pressure and for the treatment of disturbances of cerebral and peripheral blood flow.

The new active compounds can be converted in a known manner into the customary formulations, such as tablets, capsules, coated tablets, pills, granules, aerosols, syrups, emulsions, suspensions and solutions, using inert, non-toxic, pharmaceutically suitable vehicles or solvents. The therapeutically active compound, should thus, in each case, be present in a concentration of about 0.5 to 90% by weight of the total mixture, that is to say in amounts which suffice to achieve the dosage range indicated.

The formulations are prepared, for example, by extending the active compounds with solvents and/or vehicles, optionally with the use of emulsifiers and/or dispersing agents, and, for example, when using water as a diluent, organic solvents can optionally be used as auxiliary solvents Examples of auxiliaries which may be mentioned are: water, non-toxic organic solvents, such as paraffins (for example petroleum fractions), vegetable oils (for example groundnut oil/sesame oil), alcohols (for example ethyl alcohol and glycerol) and glycols (for example propylene glycol and polyethylene glycol), solid vehicles, such as, for example, natural rock powders (for example kaolins, aluminas, talc and chalk), synthetic rock powders (for example highly disperse silica and silicates) and sugars (for example crude sugar, lactose and glucose), emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl sulphate).

Administration is effected in the customary manner, preferably orally or parenterally, in particular perlingually or intravenously. In the case of oral administration, the tablets can, of course, also contain in addition to the vehicles mentioned, additives such as sodium citrate, calcium carbonate and dicalcium phosphate, together with various additional substances, such as starch, preferably potato starch, gelatin and the like. Furthermore, lubricants such as magnesium stearate, sodium lauryl sulphate and talc, can be co-used when making tablets. In the case of aqueous suspensions and/or elixirs which are intended for oral use, the active compounds can be mixed with various flavor-improving agents or colorants in addition to the abovementioned auxiliaries.

In the case of parenteral administration, solutions of the active compounds, employing suitable liquid vehicles, can be used.

In general, it has proved advantageous, in the case of intravenous administration, to administer amounts of about 0.001 to 10 mg/kg, preferably about 0.05 to 5 mg/kg of body weight daily to achieve effective results, and, in the case of oral administration, the dosage is about 0.05 to 20 mg/kg, preferably 0.5 to 5 mg/kg of body weight daily.

Nevertheless, it can at times be necessary to deviate from the amounts mentioned, and in particular to do so as a function of the body weight of the experimental animal or of the nature of the administration method, but also because of the species of animal and its individual behavior towards the medicament, and the nature of the formulation of the medicament and the time or interval over which the administration takes place. Thus, it can suffice in some cases to manage with less than the abovementioned minimum amount, while in other cases the upper limit mentioned must be exceeded. Where relatively large amounts are administered, it can be advisable to divide these into several individual administrations over the course of the day. The same dosage range is envisaged for administration in human medicine. In this connection, the above statements similarly apply.

PREPARATION EXAMPLES

Example 1

Decyl ethyl 1,4-dihydro-2,6-dimethyl-4-(3-nitrophenyl)pyridine-3,5-dicarboxylate

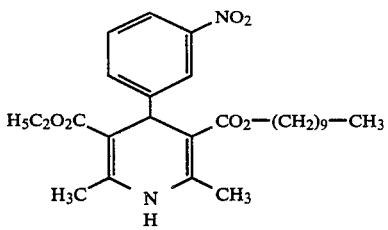

A solution of 263 g (1 mol) of ethyl 2-(3-nitrobenzylidene)acetoacetate and 241 g (1 mol) of decyl 3-aminocrotonate in 2.4 liters of absolute ethanol was heated to boiling under nitrogen for 18 hours. The mixture was then filtered hot and the filtrate was evaporated in vacuo to about one half of the volume. The concentrated solution was cooled in ice, producing a thick mass of crystals. This was filtered off with suction, recrystallized from ethanol and, after washing with 0.5 liters of n-hexane, was dried in a vacuum oven at 60° C.

Melting point: 106°-108° C.

Yield: 337 g (69.5%).

Example 2

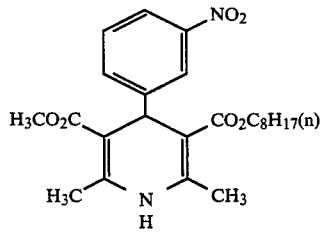

By reaction of methyl 2-(3-nitrobenzylidene)acetoacetate and octyl 3-aminocrotonate in ethanol in analogy to Example 1, methyl octyl 1,4-dihydro-2,6-dimethyl-4-(3-nitrophenyl)pyridine-3,5-dicarboxylate, of melting point 100° C. (ethanol), was obtained.

Yield: 65% of theory.

Example 3

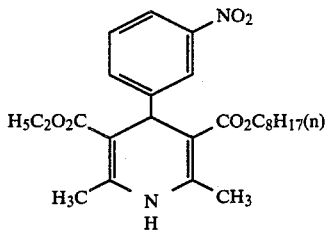

By reaction of ethyl 2-(3-nitrobenzylidene)acetoacetate and octyl 3-aminocrotonate in ethanol in analogy to Example 1, ethyl octyl 1,4-dihydro-2,6-dimethyl-4-(3-nitrophenyl)pyridine-3,5-dicarboxylate, of melting point 82° C. (methanol), was obtained.

Yield: 61% of theory.

Example 4

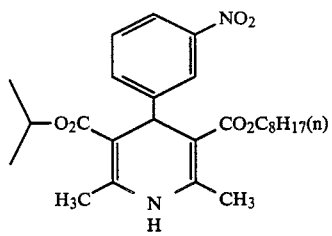

By reaction of isopropyl 2-(3-nitrobenzylidene)acetoacetate with octyl 3-aminocrotonate in ethanol in analogy to Example 1, isopropyl octyl 1,4-dihydro-2,6-dimethyl-4-(3-nitrophenyl)pyridine-3,5-dicarboxylate, of melting point 70° C. (methanol), was obtained.

Yield: 65% of theory.

Example 5

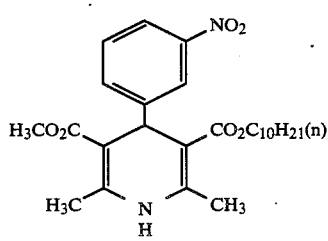

By reaction of methyl 2-(3-nitrobenxylidene)acetoacetate with decyl 3-aminocrotonate in ethanol in analogy to Example 1, decyl methyl 1,4-dihydro-2,6-dimethyl-4-(3-nitrophenyl)pyridine-3,5-dicarboxylate, of melting point 90° C. (ethanol), was obtained.

Yield: 73% of theory.

Example 6

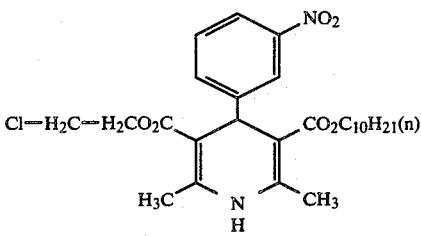

By reaction of 2-chloroethyl 2-(3-nitrobenzylidene)acetoacetate with decyl 3-aminocrotonate in ethanol in analogy to Example 1, 2-chloroethyl decyl 1,4-dihydro-2,6-dimethyl-4-(3-nitrophenyl)pyridine-3,5-dicarboxylate, of melting point 124° C. (ethanol) was obtained.

Yield: 65% of theory.

Example 7

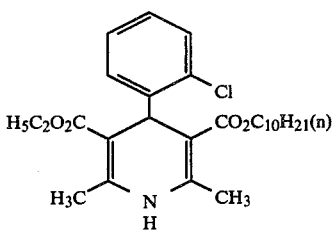

By reaction of ethyl 2-(2-chlorobenzylidene)acetoacetate with decyl 3-aminocrotonate in ethanol in analogy to Example 1, decyl ethyl 1,4-dihydro-2,6-dimethyl-4-(2-chlorophenyl)pyridine-3,5-dicarboxylate, of melting point 72° C. (methanol), was obtained.

Yield: 58% of theory.

Example 8

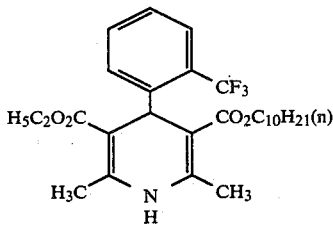

By reaction of ethyl 2-(2-trifluoromethylbenzylidene)acetoacetate with decyl 3-aminocrotonate in ethanol in analogy to Example 1, decyl ethyl 1,4-dihydro-2,6-dimethyl-4-(2-trifluoromethylphenyl)pyridine-3,5-dicarboxylate, of melting point 76° C. (methanol), was obtained.

Yield: 52% of theory.

Example 9

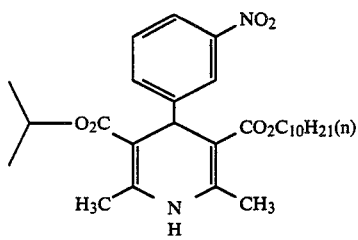

By reaction of isopropyl 2-(3-nitrobenzylidene)acetoacetate with decyl 3-aminocrotonate in ethanol in analogy to Example 1, decyl isopropyl 1,4-dihydro-2,6-dimethyl-4-(3-nitrophenyl)pyridine-3,5-dicarboxylate, of melting point 99° C. (ethanol), was obtained.

Yield: 69% of theory.

Example 10

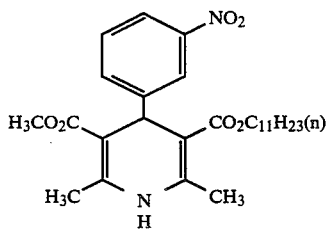

By reaction of methyl 2-(3-nitrobenzylidene)acetoacetate with undecyl 3-aminocrotonate in ethanol in analogy to Example 1, methyl undecyl 1,4-dihydro-2,6-dimethyl-4-(3-nitrophenyl)pyridine-3,5-dicarboxylate, of melting point 85° C. (ethanol) was obtained.

Yield: 78% of theory.

Example 11

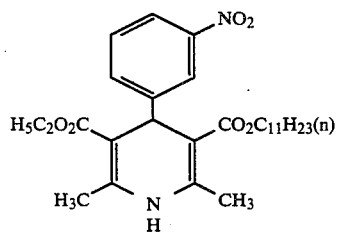

By reaction of ethyl 2-(3-nitrobenzylidene)acetoacetate with undecyl 3-aminocrotonate in ethanol in analogy to Example 1, ethyl undecyl 1,4-dihydro-2,6-dimethyl-4-(3-nitrophenyl)pyridine-3,5-dicarboxylate, of melting point 107° C. (ethanol), was obtained.

Yield: 75% of theory.

Example 12

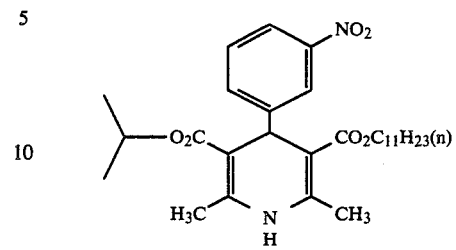

By reaction of isopropyl 2-(3-nitrobenzylidene)acetoacetate with undecyl 3-aminocrotonate in ethanol in analogy to Example 1, isopropyl undecyl 1,4-dihydro-2,6-dimethyl-4-(3-nitrophenyl)pyridine-3,5-dicarboxylate, of melting point 108° C. (ethanol) was obtained.

Yield: 69% of theory.

Example 13

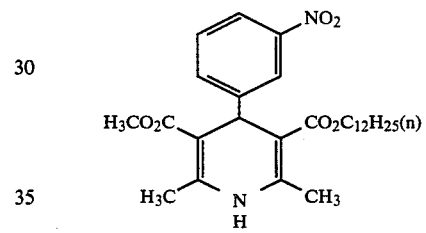

By reaction of methyl 2-(3-nitrobenzylidene)acetoacetate with dodecyl 3-aminocrotonate in ethanol in analogy to Example 1, dodecyl methyl 1,4-dihydro-2,6-dimethyl-4-(3-nitro-phenyl)pyridine-3,5-dicarboxylate, of melting point 94° C. (ethanol), was obtained.

Yield: 66% of theory.

Example 14

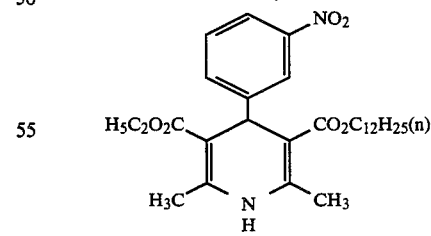

By reaction of ethyl 2-(3-nitrobenzylidene)acetoacetate with dodecyl 3-aminocrotonate in ethanol in analogy to Example 1, dodecyl ethyl 1,4-dihydro-2,6-dimethyl-4-(3-nitrophenyl)pyridine-3,5-dicarboxylate, of melting point 100° C. (ethanol), was obtained.

Yield: 76% of theory.

Example 15

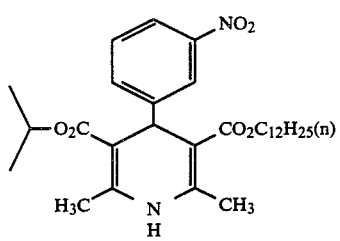

By reaction of isopropyl 2-(3-nitrobenzylidene)acetoacetate with dodecyl 3-aminocrotonate in ethanol in analogy to Example 1, dodecyl isopropyl 1,4-dihydro-2,6-dimethyl-4-(3-nitrophenyl)pyridine-3,5-dicarboxylate, of melting point 100° C. (ethanol), was obtained.

Yield: 60% of theory.

Example 16

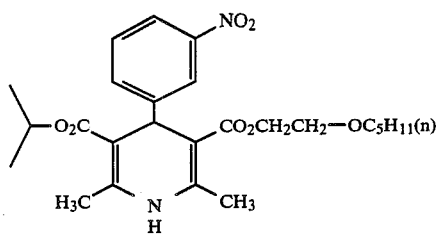

By reaction of isopropyl 2-(3-nitrobenzylidene)acetoacetate with 2-pentyloxyethyl 3-aminocrotonate in isopropanol in analogy to Example 1, isopropyl 2-pentyloxyethyl 1,4-dihydro-2,6-dimethyl-4-(3-nitrophenyl)pyridine-3,5-dicarboxylate, of melting point 75° C. (ether/petroleum ether), was obtained.

Yield: 65% of theory.

Example 17

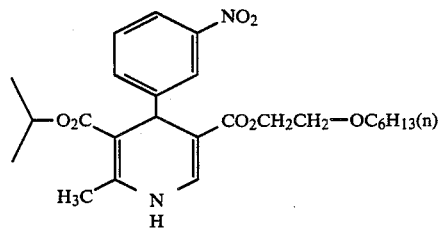

By reaction of isopropyl 2-(3-nitrobenzylidene)acetoacetate with 2-hexyloxyethyl 3-aminocrotonate in isopropanol in analogy to Example 1, 2-hexyloxyethyl isopropyl 1,4-dihydro-2,6-dimethyl-4-(3-nitrophenyl)pyridine-3,5-dicarboxylate, of melting point 83° C. (ether/petroleum ether), was obtained.

Yield: 80% of theory.

Example 18

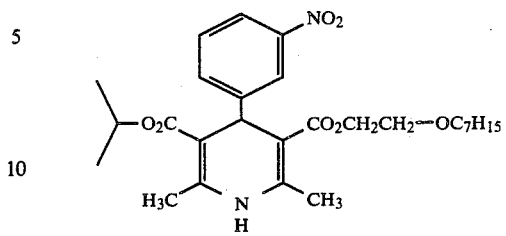

By reaction of isopropyl 2-(3-nitrobenzylidene)acetoacetate with 2-heptyloxyethyl 3-aminocrotonate in isopropanol in analogy to Example 1, 2-heptyloxyethyl isopropyl 1,4-dihydro-2,6-dimethyl-4-(3-nitrophenyl)pyridine-3,5-dicarboxylate, of melting point 80° C. (ether/petroleum ether) was obtained.

Yield: 72% of theory.

Example 19

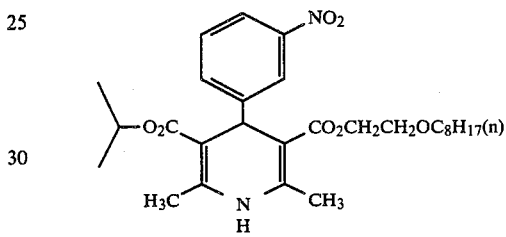

By reaction of isopropyl 2-(3-nitrobenzylidene)acetoacetate with 2-octyloxyethyl 3-aminocrotonate in isopropanol in analogy to Example 1, isopropyl 2-octyloxyethyl 1,4-dihydro-2,6-dimethyl-4-(3-nitrophenyl)pyridine-3,5-dicarboxylate, of melting point 89° C. (ether/petroleum ether), was obtained.

Yield: 76% of theory.

Example 20

5-Decyl 3-ethyl 2-amino-1,4-dihydro-6-methyl-4-(3-nitrophenyl)pyridine-3,5-dicarboxylate

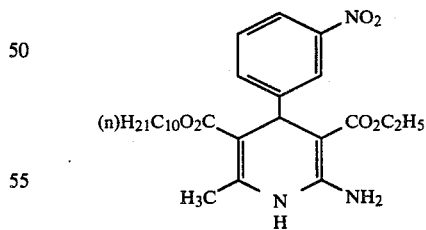

A solution of 1.15 g (50 mmol) of sodium in 100 ml of ethanol was added dropwise at room temperature, with stirring, to a solution of 18.8 g (50 mmol) of decyl 2-(3-nitrobenzylidene)acetoacetate and 8.3 g (50 mmol) of ethyl amidinoacetate hydrochloride in 250 ml of ethanol. The mixture was then heated to boiling for 15 minutes. After standing overnight, the precipitated sodium chloride was filtered off, the filtrate was evaporated in vacuo and the oily residue was brought to crystallization by trituration with ether/petroleum ether. The crude product was filtered off with suction and recrystallized from ethanol, melting point: 190°–191° C.

Yield: 65% of theory.

Example 21

5-Decyl 3-ethyl 2-amino-6-methyl-4-(3-nitrophenyl)-4H-pyran-3,5-dicarboxylate

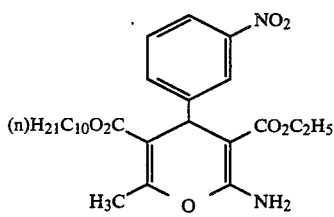

A solution of 5.7 g (15 mmol) of decyl 2-(3-nitrobenzylidene)acetoacetate and 1.8 g (15 mmol) of ethyl cyanoacetate in 15 ml of ethanol was heated to boiling in the presence of 0.3 ml of piperidine, for 4 hours. The solvent was then removed by distillation and the oily residue was purified by column chromatography (SiO$_2$, chloroform) and brought to crystalli ation, melting point: 100° C., yield: 3.3 g (45%).

It will be appreciated that the instant specification and examples are set forth by way of illustration and not limitation, and that various modifications and changes may be made without departing from the spirit and scope of the present invention.

We claim:

1. An asymmetrical compound of the formula

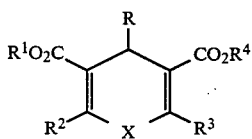

in which

R represents phenyl or naphthyl optionally containing 1 to 2 identical or different substituents from the group consisting of phenyl, alkyl, alkoxy, alkylene, dioxyalkylene, halogen, trifluoromethyl, polyfluoroalkoxy, nitro, cyano, azido and SO$_m$-alkyl (m=0 to 2), R$^1$ represents a straight-chain, branched or cyclic, saturated or unsaturated hydrocarbon radical, which is optionally interrupted by 1 oxygen atom in the chain, and/or which is optionally substituted by halogen, hydroxyl, phenyl, phenoxy, or by an amino group which in turn is optionally substituted by 2 identical or different substituents from the group consisting of alkyl having 1 to 4 carbon atoms, phenyl and benzyl, R$^4$ represents a straight-chain, branched or cyclic, saturated or unsaturated aliphatic hydrocarbon radical having 7 to 14 carbon atoms, which is optionally interrupted by one oxygen atom and/or which is optionally substituted by halogen or hydroxyl, R$^2$ and R$^3$ are identical or different and each represent hydrogen, a straight-chain or branched alkyl radical, a phenyl radical or a benzyl radical, or, for the case where one of the substituents R$^2$ or R$^3$ has the above-mentioned meaning, the other represents hydroxymethyl, acetoxymethyl or amino, and X represents N—R$^5$, wherein R$^5$ represents hydrogen, a straight-chain or branched alkyl radical, which is optionally interrupted by an oxygen atom, a phenyl radical or a benzyl radical, or a pharmaceutically acceptable acid addition salt thereof.

2. A compound according to claim 1, in which

R represents phenyl, the phenyl ring optionally being substituted by one or two identical or different substituents from the group consisting of phenyl, alkyl having 1 to 4 carbon atoms, alkoxy having 1 to 2 carbon atoms, fluorine, chlorine, bromine, trifluoromethyl, trifluoromethoxy, difluoromethoxy, nitrol, cyano, axido or alkylmercapto having 1 to 4 carbon atoms in the alkyl radical, R$^1$ represents a straight-chain branched or cyclic, saturated or unsaturated hydrocarbon radical having up to 14 carbon atoms, which is optionally interrupted by an oxygen atom and/or is optionally substituted by fluorine, chlorine, hydroxyl or amino, R$^4$ represents a straight-chain, branched cyclic, saturated or unsaturated aliphatic hydrocarbon radical having 10 to 12 carbon atoms, which is optionally interrupted by an oxygen atom in the chain and/or is optionally substituted by fluorine, chlorine or hydroxyl, R$^2$ and R$^3$ are identical or different and each represent hydrogen, alkyl having 1 to 2 carbon atoms, phenyl or benzyl or one of the substituents R$^2$ or R$^3$ represents a hydroxymethyl, acetoxymethyl or amino group, the other substituent having the previously mentioned meaning, X represents N—R$^5$, wherein R$^5$ represents hydrogen, an alkyl radical having up to 4 carbon atoms, which is optionally interrupted by an oxygen atom, a phenyl radical or a benzyl radical.

3. A compound according to claim 1, in which

R represents a phenyl radical which contains one or two identical or different substituents from the group consisting of chlorine, trifluoromethyl, nitro or cyano, R$^1$ represents a straight-chain or branched hydrocarbon radical having up to 7 carbon atoms, which is optionally interrupted by an oxygen atom in the chain and/or is optionally substituted by fluorine or chlorine, or by an amino group which in turn is optionally substituted by two methyl groups or by a methyl and a benzyl group, R$^4$ denotes a straight-chain, branched or cyclic, saturated or unsaturated aliphatic hydrocarbon radical having ten to twelve carbon atoms, which is optionally interrupted by an oxygen atom in the chain or is optionally substituted by fluorine, chlorine or hydroxyl, R$^2$ and R$^3$ each represent hydrogen or an alkyl radical having 1 to 2 carbon atoms, or one of the substituents R$^2$ or R$^3$ represents the amino group, in which case the other substituent has the abovementioned meaning, and X represents N—R$^5$, wherein R$^5$ represents a hydrogen atom or an alkyl radical having up to 3 carbon atoms.

4. A compound according to claim 1, in which $R^4$ denotes a straight-chain, branched or cyclic saturated or unsaturated aliphatic hydrocarbon radical having 10 carbon atoms, which is optionally interrupted by an oxygen atom in the chain or is optionally substituted by fluorine, chlorine or hydroxyl.

5. A compound according to claim 1, wherein such compound is decyl ethyl 1,4-dihydro-2,6-dimethyl-4-(3-nitrophenyl)-pyridine-3,5-dicarboxylate of the formula

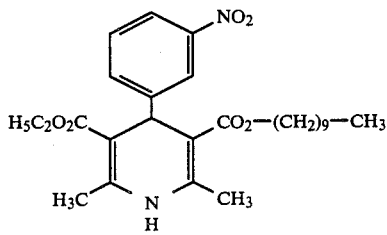

or a pharmaceutically acceptable acid addition salt thereof.

6. A compound according to claim 1, wherein such compound is decyl methyl 1,4-dihydro-2,6-dimethyl-4-(3-nitrophenyl)pyridine-3,5-dicarboxylate of the formula

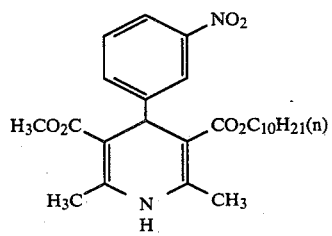

or a pharmaceutically acceptable acid addition salt thereo.

7. A compound according to claim 1, wherein such compound is decyl ethyl 1,4-dihydro-2,6-dimethyl-4-(2-trifluoromethylphenyl)pyridine-3,5-dicarboxylate of the formula

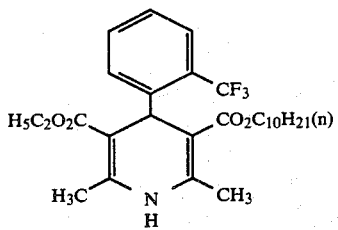

or a pharmaceutically acceptable acid addition salt thereof.

8. A compound according to claim 1, wherein such compound is methyl undecyl 1,4-dihydro-2,6-dimethyl-4-(3-nitrophenyl) pyridine-3,5-dicarboxylate of the formula

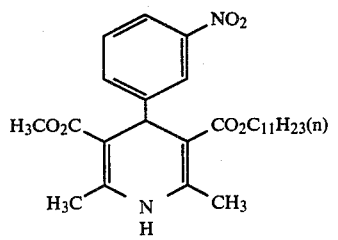

or a pharmaceutically acceptable acid addition salt thereof.

9. A hypotensive composition comprising a hypotensive amount of a compound or salt according to claim 1 in admixture with a pharmaceutically acceptable diluent.

10. A composition according to claim 9, in the form of tablets, pills, dragees, capsules, ampules or suppositories.

11. A method of lowering blood pressure in human and non-human animals which comprises administering to such animal a hypotensive amount of a compound or salt according to claim 1.

12. A method according to claim 11, wherein such compound is
decyl ethyl 1,4-dihydro-2,6-dimethyl-4-(3-nitrophenyl)-pyridine-3,5-dicarboxylate,
decyl methyl 1,4-dihydro-2,6-dimethyl-4-(3-nitrophenyl)pyridine-3,5-dicarboxylate,
decyl ethyl 1,4-dihydro-2,6-dimethyl-4-(2-trifluoromethylphenyl)pyridine-3,5-dicarboxylate or
methyl undecyl 1,4-dihydro-2,6-dimethyl-4-(3-nitrophenyl)pyridine-3,5-dicarboxylate
or a pharmaceutically acceptable acid addition salt thereof.

* * * * *

UNITED STATES PATENT AND TRADEMARK OFFICE
CERTIFICATE OF CORRECTION

PATENT NO. : 4,622,332

DATED : Nov. 11, 1986

INVENTOR(S) : Egbert Weninger, et al.

It is certified that error appears in the above-identified patent and that said Letters Patent is hereby corrected as shown below:

| | |
|---|---|
| Col. 2, line 65 | After "$R^{3'}$" insert --$R^4$-- |
| Col. 4, lines 17, 38 | Delete "Reacting" and substitute --reacting-- |
| Col. 12, line 14 | Correct spelling of --According-- |
| Col. 13, line 44 | Delete "2 3" and substitute --2,3-- |
| Col. 14, line 16 | After "solvents" insert --.-- |
| Col. 23, line 61 | Correct spelling of --nitrobenzylidene-- |
| Col. 29, line 60 | Delete "7" and substitute --10-- |
| Col. 30, line 16 | Delete "nitrol" and substitute --nitro-- |

Signed and Sealed this

Thirty-first Day of March, 1987

Attest:

DONALD J. QUIGG

Attesting Officer

Commissioner of Patents and Trademarks